United States Patent [19]

McConnell et al.

[11] Patent Number: 4,737,464

[45] Date of Patent: Apr. 12, 1988

[54] SOLID-STATE OPTICAL ASSAY IMAGING APPARATUS

[75] Inventors: Harden M. McConnell, Stanford; Jonathan Briggs, Palo Alto, both of Calif.; John W. Parce, Winston-Salem, N.C.

[73] Assignee: Molecular Devices Corporation, Palo Alto, Calif.

[21] Appl. No.: 780,485

[22] Filed: Sep. 26, 1985

[51] Int. Cl.[4] .......................................... G01N 21/00
[52] U.S. Cl. ..................................... 436/43; 422/67; 422/73; 422/68; 358/213; 436/164; 436/805; 436/807
[58] Field of Search ..................... 422/63, 65, 67, 72, 422/73, 68; 436/47, 43, 805, 807; 356/127, 246; 358/213

[56] References Cited

U.S. PATENT DOCUMENTS

| | | | |
|---|---|---|---|
| 3,464,799 | 9/1969 | Kimbell | 422/91 |
| 4,276,051 | 6/1981 | Ginsberg et al. | 422/64 |
| 4,344,091 | 8/1982 | Gardner et al. | 358/213 |
| 4,441,125 | 4/1984 | Parkinson | 358/213 |
| 4,465,938 | 8/1984 | Kato et al. | 356/246 |
| 4,536,369 | 8/1985 | Sakarada et al. | 436/47 |
| 4,539,296 | 9/1985 | Manabe | 436/47 |
| 4,549,809 | 10/1985 | Minekane et al. | 422/65 |
| 4,550,084 | 10/1985 | Nelson et al. | 356/427 |
| 4,580,895 | 4/1986 | Patel | 422/73 |
| 4,601,575 | 7/1986 | Tamaki | 356/127 |
| 4,621,063 | 11/1986 | Wyatt | 422/73 |

Primary Examiner—Michael S. Marcus
Attorney, Agent, or Firm—Bertram I. Rowland; Steven F. Caserza

[57] ABSTRACT

An apparatus for determining a characteristic of a signal modulating component related to an analyte of interest at an assay site by measuring light modulated by the component. A light source uniformly illuminates the assay site and a reference site. The light is directed from the sites onto a group of memory cells on the surface of a random access memory. The memory cells will decay from a logical 1 to a logical 0 due to the light over a period of time which is a function of the intensity of the light and the reference voltage of the memory cells marking the difference between a 1 and a 0. The digital state of each of the memory cells in the group is measured a predetermined exposure time. The measured states of a group of memory cells corresponding to the assay site are compared to the memory cell states for a reference group. The measured states are then analyzed to determine a characteristic of the analyte.

13 Claims, 4 Drawing Sheets

SOLID-STATE OPTICAL ASSAY IMAGING APPARATUS

BACKGROUND OF THE INVENTION

The present invention relates to apparatuses for determining a characteristic of an analyte by measuring light modulated by the analyte.

The desire to measure an increasingly complex array of materials in a broad spectrum of environments is ever increasing. For example, since the advent of radioimmunoassay in the 1950's, a large number of additional protocols have been developed for measuring a large number of physiologically active compounds. As biochemistry and molecular biology have rapidly advanced, numerous compounds have been added to an already extensive list. Toward this end, there have been increasing efforts to develop new techniques and new apparatuses for rapid easy determination of analytes of interest.

The disciplines involved in the development of assays and apparatuses for measuring the assay results are quite diverse. Chemistry, physics, immunology, enzymology, and electronics are only a few of the disciplines which have found application in the field of chemical assays. Therefore, it is not always apparent that devices which find application in one field can be modified to be useful in a different field.

For many applications, a light-modulating sample spot is produced on a surface, for example, a paper surface. The light might be modulated by the spot absorbing light, reflecting light, scattering the light, causing fluorescence, or otherwise affecting the light. This change in a property of the light will be indicative of a characteristic of a signal generating compound in the spot. The light can be sensed with any number of devices, such as charge coupled devices, charge-injection devices, such as charge coupled devices, charge-injection devices, or photodiodes. These devices operate according to photoelectric effects by producing an electrical response in proportion to the amount of light impinging on the device. This analog signal can be sampled to determine the amount of light impinging upon the device. These analog values can be converted into digital value with an A/D (analog to digital) converter so that the data may be analyzed by a computer. The actual value of the signal can be measured or the amount of time required to reach a specified signal can be measured to determine the amount of light impinging on the device.

Outside the chemical field in the area of image processing, a recent development is the use of the optical dynamic RAM (random access memory) for image processing. A dynamic RAM has a series of memory cells with each cell acting like a storage capacitor. The storage capacitor will either have a voltage stored on it, voltages above or below a reference level indicated as a digital 1 or 0 value, respectively. Because leakage current causes the voltage on a capacitor to decay, each memory cell is periodically refreshed in a dynamic RAM to maintain the integrity of the data. If the surface of the RAM is exposed to light, this light will cause a photocurrent which will produce an additional leakage of current. The amount of light impinging on the RAM can be determined by measuring the amount of time for each memory cell to decay from a logical 1 to a logical 0.

Description of the Relevant Literature

The optical use of a dynamic RAM is described in U.S. Pat. No. 4,441,125, which disclosure is incorporated herein by reference.

SUMMARY OF THE INVENTION

The present invention is an apparatus for determining a characteristic of a signal modulating or generating component related to an analyte of interest at an assay site by measuring light modulated by the signal modulating component. A light source uniformly illuminates one or more assay sites and a reference site or where the illumination is nonuniform, a correction can be provided in a program which corrects for the nonuniformity. The light is directed from the sites onto a group of memory cells on the surface of the random access memory. The memory cells will decay from a logical 1 to a logical 0 due to the light over a period of time which is a function of the intensity of the light and the reference voltage of the memory cells marking the difference between a 1 and a 0. The digital state of each of the memory cells in the group is measured after a predetermined exposure time. The measured states of a group of memory cells corresponding to the assay site are compared to the memory cell states for a reference group. The measured states are then analyzed to determine the signal from the signal modulating component which may then be related to a characteristic of the analyte.

In one embodiment, the digital state of the memory cells is measured periodically and the amount of time for fifty percent of the cells to change from a digital 1 to a digital 0 is determined. This amount of time is compared to a standard value, such as the amount of time for the light to cause fifty percent of the memory cells to change state in the absence of any signal modulating component. A characteristic of the analyte is then determined from the two different times.

In another variation, the reference level of the memory cells can be varied to vary the sensitivity of the RAM. This reference level is the voltage value between typically 0 and 5 volts, which is used as an indication of whether a particular voltage will be considered a digital 0 (below the reference value) or a digital 1 (above the reference value). The reference level at which 50% of the memory cells become discharged within a specified time can then be determined.

The present invention thus provides a direct digital indication of the amount of light from a site, in contrast to prior art devices which utilized an analog measurement of the light to provide values which could be converted into digital values for analysis by a computer. The present invention uniquely recognizes that properties of chemical analytes, usually by direct or indirect interaction with a signal modulating component, can be measured with the required sensitivity utilizing the digital optical RAM and varying either the reference level or the times at which measurements are taken to produce a gray scale.

By designating a different block of memory cells for each of a plurality of assay sites, a plurality of results can be reported substantially simultaneously. Inhomogeneities in the sample are compensated for by averaging the values of all the memory cells in a block.

Figure 1:
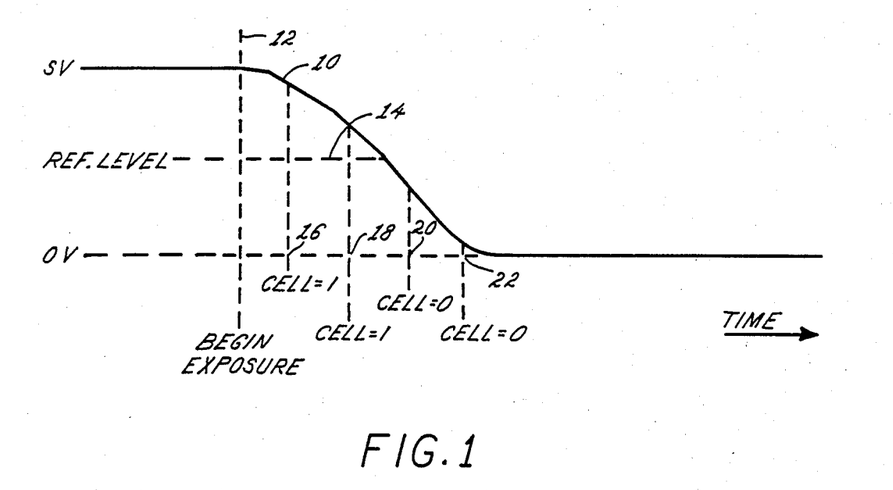
FIG. 1 is a graphical representation of the voltage on a memory cell of the present invention.

FIG. 1 shows a graphical representation of the voltage of a single memory cell of an optical RAM. The voltage level 10 starts at 5 volts and decays over time to 0 volts due to the leakage of photocurrent caused by light impinging upon the memory cell. This leakage due to light commences when light is turned on at a time 12. Leakage due to other sources is also present, and preferably the memory cell is refreshed to 5 volts immediately before the light is turned on. An exposure can commence by turning on a light or, preferably, by refreshing the memory cells to a logical 1 with the light already turned on. A readout of the memory cell will indicate a logical 1 as long as the voltage value is above a reference level 14. When the voltage level falls below the reference level 14, the memory cell will indicate a logical 0. As shown, readings are made at times 16, 18, 20, and 22. Time 20 is the first time at which a reading of logical 0 is obtained, since the voltage has fallen below reference level 14. By determining the amount of time between time 12 and time 20 (or more generally between the start of the exposure and the point at which the bit voltage falls below the reference level), the amount of light impinging on the cell can be determined and can be compared to a similar measurement for a control value. This control value could be, for instance, the amount of light absorbed or reflected or otherwise modulated by a blank paper alone, or other solid or semi-solid support upon which the signal generating compound to be measured will be placed. It could also be an assay site involving a known amount of analyte.

As can be seen, the accuracy of the time measurement can be improved by increasing the number of readings. An alternate method would be to vary the reference level 14 at a fixed time from time 12 until an indication of logical 0 is obtained.

Figure 2:
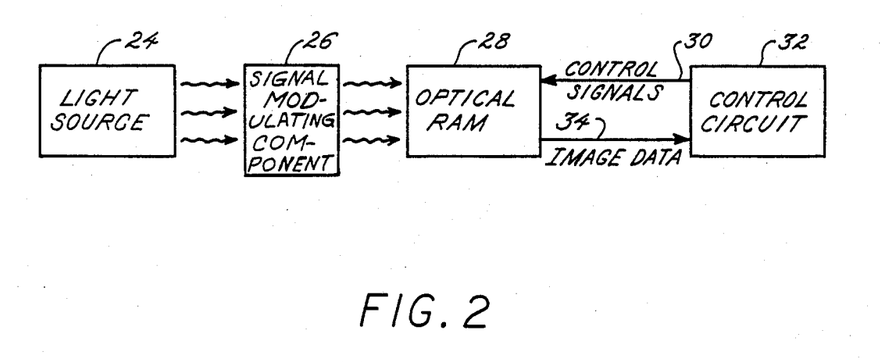
FIG. 2 is a block diagram of a specific embodiment of a system for performing the method of the present invention.

FIG. 2 is a block diagram of a preferred embodiment of the present invention. The light source 24 shines light on a signal modulating component 26. Light from signal modulating component 26 is detected by an optical RAM 28. Optical RAM 28 is controlled by control signals 30 from a control circuit 32. Image data from optical RAM 28 is provided to control circuit 32 along a data line 34.

Figure 3:
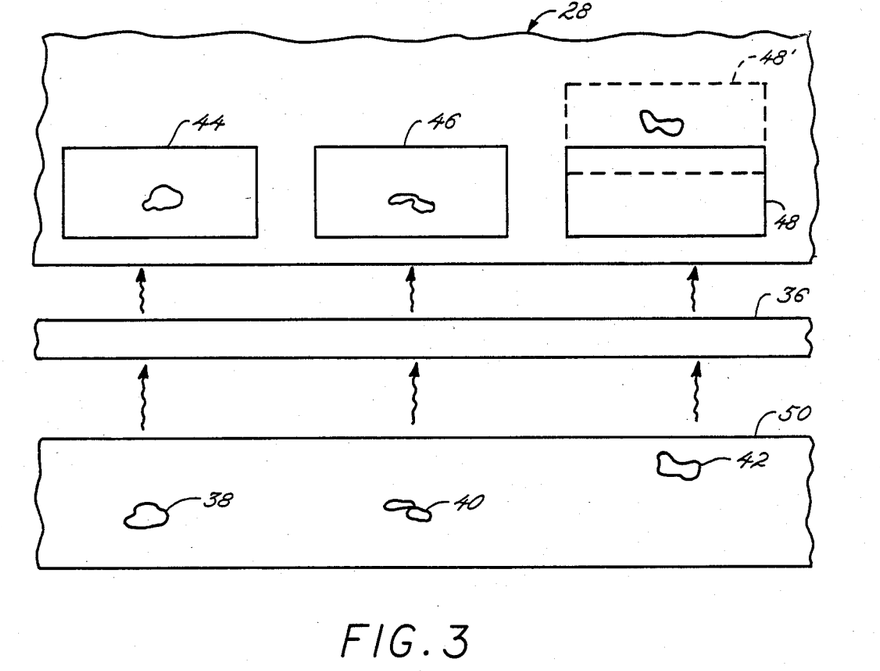
FIG. 3 is a diagram showing a portion of the optical RAM of FIG. 2 with the addition of a lens for focusing light on the optical RAM, and showing images from a plurality of sites being read by associated portions of the optical RAM.

A portion of the system of FIG. 2 is shown in FIG. 3 with the addition of a lens 36 for focusing the light on optical RAM 28. Light emanating from a series of spots 38, 40, and 42, resulting from assays with the samples containing an analyte to be determined, passes through lens 36 to produce an image of the spots on three blocks of memory 44, 46, and 48.

As can be seen, the present invention allows for the quantification of homogeous or inhomogeneous deposits of materials. For instance, if the area of spots 38 and 40 are the same, and they are equally dense, equal readings will be produced from memory blocks 44 and 46 because light will be increased or decreased over the same number of memory cells. In addition, variations in spot density which cause variations in the amount of light impinging on the same number of memory cells can be monitored by comparing the amount of time required for a particular memory cell to change from a logical 1 to a logical 0. If a spot is light absorbing, a denser spot will require more time to cause a memory cell to change from 1 to 0 than a less dense spot.

Each of blocks 44, 46, and 48 is an array of between 10 and 1000 memory cells, typically between 64 and 256 memory cells. The samples of assay media may be placed so that their images are contained within such a block of memory cells and do not overlap the boundaries of such block. If a sample should be misplaced, such as sample 42, this can be compensated for. Upon detection of no change in the light in block 48, and the detection of a change in light (as indicated by memory cells changing from a logical 1 to a logical 0) in memory cells adjacent to block 48, the computer can redesignate the memory cells adjacent group 48 to be the block for image 42 as designated by block 48'. There are many such "find a spot" routines known in the art of pattern analysis.

The light source can provide direct, indirect, or collimated light on or through the sample assay medium to provide light incident on the optical RAM surface. Preferably, the sample should be illuminated with diffuse light because it gives the best contrast. When trying to sense changes in the amount of light absorbed by the sample assay medium, the optical RAM should be arranged so that it does not receive directly reflected light from the sample assay medium substrate 50 which would produce a large background.

Depending upon the nature of the surface, the light source may be above or below the surface. The light may be monochromatic or polychromatic, usually polychromatic. A plurality of LEDs may be employed. Alternatively, fluorescent light or incandescent light may be employed.

By using a block of memory cells, in addition to the ability to integrate inhomogeneities at the assay site as described above, differences in light sensitivities of the individual memory cells are washed out to give a more efficient determination of a result. The value obtained may be compared with a standard which could be the value of light from the solid support 50 for the samples, an assay site where a known amount of analyte is present, or any combination thereof or other standard.

The photosensitive surface of optical RAM 28 is protected by a transparent plate in front of the photosensitive surface. The plate should be of optical quality so as to allow for substantially complete transmission of light of the wavelength range of interest through the plate. For some applications, the plate should be nonreflective, being coated with an antireflection coating on both surfaces according to standard procedures. The thickness of the transparent plate is not critical to the subject invention and is primarily one of convenience, where mechanical integrity and high optical quality will be the primary constraints.

Normally, the assays will be carried out on a rigid usually solid support 50 although semi-solid supports, e.g., gels, may find application. The soild support may be transparent, translucent, or opaque, where the signal generating component, in the assay medium, modulates the amount of light emanating from the surface to the detector. This may result from changes (induced by the assay) in the absorptivity, reflectivity, scattering or fluorescence of the surface. For the most part, the assay array will be a plurality of sites distributed over some area. A 64 K bit optic-RAM typically has two arrays each with a rectangular shape where the ratio of the length of the sides is about 5:1. It will therefore be necessary that the light incident on the dynamic RAM should be appropriately distributed over the surface of the dynamic RAM. This can typically be done by lens 36, though in some applications direct illumination may be used. Various optical systems are known which can be used to change the pattern of light incident on the dynamic RAM.

The apparatus which is employed has means for positioning the assay medium support material in proper relationship to the detector. The assay may be carried out in accordance with a wide variety of protocols and on a wide variety of surfaces. Thus, various materials, such as translucent, transparent, or opaque fibrous surfaces, such as cellulose, nitrocellulose, etc., glass or plastic surfaces, or the like may be employed. The surfaces may be associated with various solid supports, container devices, such as microtiter plates, well holders, multiple pipetters, and the like.

The assays may be employed to determine various characteristics of an analyte. The characteristics may include absolute amount, concentration, distribution, nature of the surface, chemical reactivity, response to physical stimulus, e.g., light, or the like.

The analyte may be any substance, mixture of substances or assemblage of substances. The analyte may be an organic or organometallic molecule, such as naturally occurring or synthetic drugs, chemicals, or polymers, assemblage, such as viruses and cells, or the like. Analytes of interest include synthetic drugs, naturally occurring physiologically active compounds, fragments or whole viruses and cells, e.g. microorganisms, plant, insect, mammalian, etc., or components thereof, commercial compounds, or the like. The assay may be employed for detecting a naturally occurring or synthetic compound, or a virus or cell in a physiological fluid, a component of a naturally occurring stream or process stream, a component of interest in the environment, in plants, or the like.

In carrying out the assays, the sample is combined with various reagents either concomitantly or sequentially, with the result that a light responsive material becomes bound to a surface or in some way interacts with the surface or a light responsive material bound to the surface. The light responsive material may be, for example, a light-absorbing dye, enzyme product, product of a chemical reaction, a fluorophore, a small metallic particle, or the like. The significant factor is that the signal (the light impinging on the optical RAM in relation to a particular assay medium site) is related to the amount of analyte in the sample.

As a result of the assay, the amount of signal generating component could modulate the light in any number of manners. For instance, a dye could be bleached to decrease the light absorption. Alternatively, a metallic substance may become bound, causing an assay site to be more reflective. Other procedures may affect the texture of the sample, making it more grainy and changing the scattering properties of the surface. Or, the surface may become fluorescent or the light transmitted may be modulated in any other manner.

In many instances, one or more reagents are bound to the surface and binding occurs by complex formation between ligands and receptors, e.g., antigens and antibodies, or complementary nucleic acid sequences. Where dyes or fluorophores are involved, normally there will be a plurality of dye molecules associated with each analyte molecule, so as to have an amplification of signal. Preferably, one employs a catalyst, particularly an enzyme catalyst, which provides a plurality of signal-producing molecules for each analyte molecule. For example, one reagent could contain conjugates of an enzyme and a member of a specific binding pair comprised of ligand and receptor or complementary nucleic acid sequences. One can use either competitive or noncompetitive assays, where the analyte competes for the homologous binding member with the enzyme conjugate or the analyte provides a bridge between the complementary binding member bound to the surface and the complementary member-enzyme conjugate. After incubating the assay mixture for a sufficient time for complex formation between homologous binding members, non-specific binding enzyme may be washed away and a development solution added to the assay site, where any enzyme present catalyzes the reaction which results in the signal generating component which serves as a light modulating product.

Single or multiple measurements may be made at an assay site. The determined value may be an end point determination, a single determination at a predetermined time point, or two or more determinations may be made and the rate or kinetics of formation or destruction of the signal generating component determined.

Devices are also available where a paper surface is employed supported by an absorbing medium and the sample and various reagents are placed sequentially at a specific spot. The presence of the analyte prevents the enzyme conjugate from being absorbed by the absorbing medium underneath, so that the enzymatic reaction occurs at the surface when the developing reagents are added.

A large number of assay protocols exist which may be used or adapted for use in the subject invention. These protocols may involve carrying out the assay in a separate medium and transferring the assay medium to the substrate, performing a fraction of the protocol of the assay away from the substrate and completing the assay protocol on the substrate, or the entire protocol may be performed on the substrate, where only the sample need be added.

Many of the determinations will involve specific binding pair member-complex formation, e.g., complex of ligand and receptor, where one of the members of the complex is labeled or serves as a site to which a label may be bound. For example, biotinylated antibody can be used to detect a ligand and avidin labeled with a dye or fluorescein can be used to label the complex. Usually, the methods will involve complex formation where the presence of the complex results, directly or indirectly, in binding of the label to a support. Where the label is a light responsive or modulating material, e.g., light absorptive or reflective, fluorescent, etc., no additional reagents will be required. Where the label does not modulate the light transmitted directly, e.g., the label produces a product which modulates the transmitted light, e.g., enzyme with light modulating product, then additional reagents are required.

The following are a few illustrative protocols which may be employed. For determining an antibody to a ligand (antiligand), a ligand-enzyme conjugate may be prepared where binding of antiligand to the ligand-enzyme conjugate results in inhibition of enzyme activity. The ligand-enzyme conjugate may be bound to the substrate. Where a plurality of antibodies are of interest, e.g., a serotype of a pathogen, different ligand enzyme conjugates may be affixed at different sites on the substrate. The sample may be diluted with enzyme substrate, where the enzymatic product is colored, and the solution applied to the various sites. After a predetermined time a reduction in color intensity in comparison to a standard would be indicative of the presence of the antiligand. By comparing the light transmitted from each site with a standard (a site to which antibody does not bind could be used as a standard) the serotype could be readily detected. This method provides a number of advantages in that a plurality of determinations are carried out simultaneously under substantially identical conditions, so that any differences should be solely a function of the analyte. Furthermore, in an assay where complex formation between the ligand and antiligand occurs in only one or a few instances, the large number of negative results can be averaged and serve as an accurate standard for a negative result. Inconsistencies in the results will also be detectable, indicating that the assay should be rerun.

Another protocol may involve detecting one or more drugs of abuse in a blood, serum or urine sample. In this case the sample could be combined with a mixture of conjugates of an enzyme with antibodies to the drugs of interest (antidrug). After incubating the mixture, a known volume of the assay sample could be transferred to a plurality of sites on a substrate. To each site would be bound a different drug of interest. The amounts of the various enzyme-antidrug conjugates would be adjusted so that, in the absence of drug in the sample, the same level of signal generating compound would be produced at each site. After incubating the sample on the substrate to permit all available antidrug sites to bind to the substrate-bound-drug, the nonspecifically bound enzyme-antidrug conjugate is washed away and enzyme substrate added. A non-fluorescent substrate which forms a fluorescent product, e.g., umbelliferyl phosphate, is added and the rate of reaction determined by the increase in fluorescence. The method has many advantages in providing multiple assays under substantially identical conditions, internal standards, simultaneous uniform washings and rapid reading. Thus, in an emergency situation one need only take a small single sample and a large number of drugs may be screened in a single set of manipulative steps.

In many instances contacting and washing may involve dipping the substrate into the medium, employing a multi-pipetter-diluter for applying the solution, or having wicking or capillary systems which provide automatic quantitative measurement. Therefore, the individual steps can be uniformly carried out with minimum technician involvement and the system allows for subtracting errors which will be of uniform occurrence.

In carrying out the assays, the apparatus may rely on one or more standards. One standard to check the electronics is the dark current, where a block is shielded from the light. Another standard is to have a blank site which has not been treated with the sample or any of the reagents. A third standard is to have one or more sites which have been treated with a sample containing a known amount of the analyte and the reagents. Or, no standard may be used when it is known that there will be a plurality of negative or positive results of known value. By employing one or more of the standards, the observed values with samples can be related to the standards to provide for a more accurate determination. Where a plurality of samples having known amounts of analyte are provided as a standard, the computer can provide for a standard curve and directly translate observed values to a concentration or weight of analyte.

The subject method may be employed with various other systems, such as electrophoresis. In electrophoresis, a thin gel is employed where components of a system may be separated by charge, weight and shape. One can then detect the various components in the gel employing reagents, such as intercalating dyes, nucleic acid probes, specific binding pair members, or the like, conjugated to enzymes or dyes. The light absorbency can then be obtained in the same manner as described above.

Figure 4A:
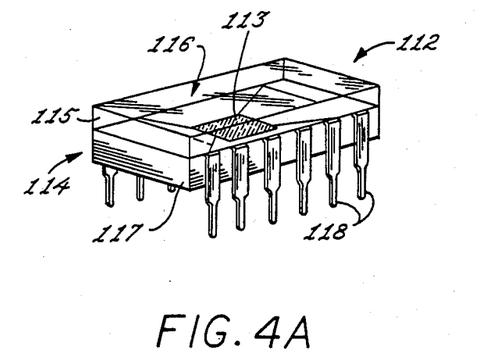
FIG. 4a depicts a packaged dynamic RAM employed as part of the detector system of the subject invention.
Figure 4B:
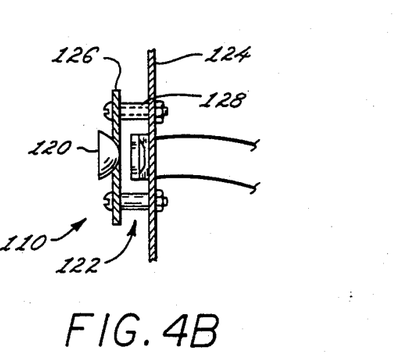
FIG. 4b schematically depicts the packaged dynamic RAM in FIG. 4a including a lens system.

Referring now to FIGS. 4a and 4b, the detector 110 involves a dynamic RAM system 112, including semiconductor chip 113, supported within a semiconductor package 114. The package 114 includes a top 115 having a clear or transparent portion 116, a film or plate transparent in at least one wavelength or wavelength range of interest. The transparent portion 116, will be referred to as a plate. The plate 116 will have an optically flat surface and may be treated to be antireflective.

Except for the clear plate 116, the package 114 is conventional. It includes a solid, clear or opaque base 117 having pins 118 extending from the base 117 for electrical interconnection to the RAM system 112. The chip 113 is mounted in the base 117 in a conventional manner and is bonded to the pins 118 in a conventional manner.

The detector 110 also includes one or more lenses 120 as shown in FIG. 4b. Lens 120 is an elliptical lens and is positioned in proper relationship to the package 114 by support structure 122. The support structure 122 includes a printed circuit board 124 on which the package 114 is mounted. The lens 120 is secured to a bracket 126 which in turn is mounted to the board 124 by connectors 128. The lens 120, the clear plate 116 and the RAM system 112 are maintained in a predefined orientation. The RAM system 112 underies the clear plate 116 and the lens 120 overlies the clear plate 116, so as to display the array of assay sites onto the RAM in appropriate spatial disposition.

For further sensitivity, a dynamic/active/restore sense amplifier employing mid-point digit line may be used. This technique is generally described in Foss, "Dynamic Memories," ISSCC Digest of Technical Papers, pp. 140–141, 1979. See also, U.S. Pat. Nos. 4,291,392 and 4,397,002, which are hereby incorporated by reference.

Figure 5:
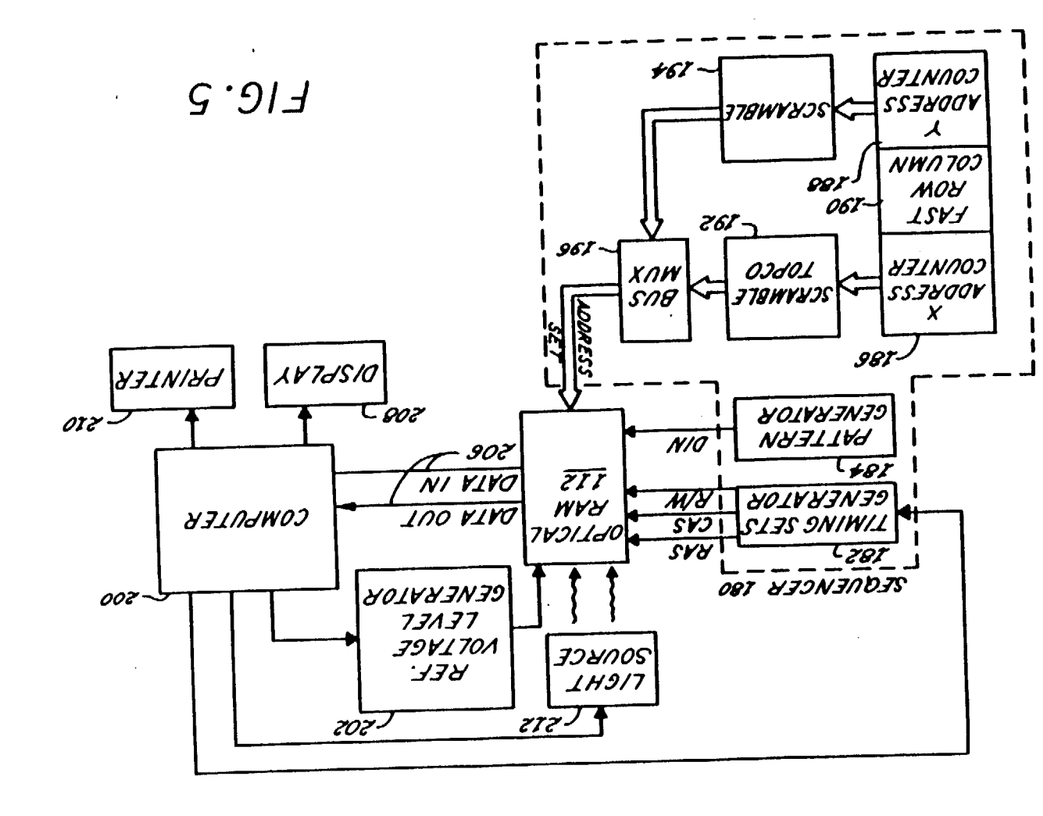
FIG. 5 is a block diagram showing an optical RAM receiving light to be evaluated, together with appropriate circuitry for controlling the optical RAM and for analyzing the data received from the optical RAM.

In FIG. 5, an embodiment of the RAM system 112 is shown as a generalized circuit schematic. This generalized circuit schematic is not conventional but is particularly adapted for the present invention. The RAM system 112 is of the type embodying associated peripheral interface, drive, and cell threshold/sense amplifier circuitry which is relatively light-insensitive compared to the memory cells in the RAM. As depicted, the RAM system 112 employs a dynamic/active/restore sense amplifier as described in the aforementioned Foss article and the referenced patents.

A commercial embodiment which is suitable as the RAM system 112 is the 1S32 OpticRAM ™ manufactured and sold by Micron Technology, Inc. of Boise, Idaho.

As an image of the assay result is focused onto the RAM 112, the memory storage capacitors in the RAM selectively discharge in accordance with the intensity of light impinging on the memory cell array. Reading out the charged states of the memory cell capacitor as a charged or discharged block provides an indication of the light intensity impinging upon the memory cells from the assay site.

An alternate method of operating the RAM system 112 as an image sensor is to read the storage cells less frequently so that they see the image longer. For example, if the array is serially read using a 1 microsecond period, every cell is read every 0.065 seconds. This means that approximately 15.4 times per second the cell is exposed to the image, reset to 5 volts, and allowed to decay for 0.065 seconds. Then, as a function of the light on it, it is read out as a logic 1 (not enough light on that cell to discharge it) or as a logic 0 (enough light to reduce the cell from 5 volts to at least 2.2 volts or less). By extending the chip read period to 10 microseconds so that it takes 0.65 seconds to scan the whole array before returning to a given memory cell, the image impinges upon a given cell 10 times longer, and the light intensity may be 1/10th that of the value previously necessary to lower a memory cell from a logic 1 to a logic 0.

Referring now to FIG. 5, a sequencer 180 is shown for operating the RAM 112 according to the invention. The sequencer 180 may take the form of a Teledyne J387A or equivalent memory tester. FIG. 5 is a functional block diagram to explain one suitable sequencer 180.

Sequencer 180 includes a timing generator 82 and a pattern generator 184. Timing generator 182 is connected to RAM 112 to produce the appropriate timing signals, including the Read/Write signal (R/W), the Column Address Strobe (CAS) signal and the Row Address Strobe (RAS) signal.

Pattern generator 184 produces a pattern which allows sequential reading of the memory cells 148 on the Data out pin of RAM 112.

Sequencer 180 also includes circuitry for providing the addresses necessary to address the various memory cells 148. A pair of X and Y address registers, 186, 188, respectively, are provided. Registers 186, 188 are coupled by a fast column/slow row sequencer 190. The respective outputs of counters 186, 188 are scrambled by scramblers 192, 194 which in turn are multiplexed onto a bus 196. Multiplex bus 196 communicates the address signals to RAM 112 via the address inputs 198.

The operation of sequencer 180 is controlled by a computer 200. Computer 200 also provides a signal to a voltage reference level generator 202 which provides a latch signal 204 to RAM 112 to select the appropriate voltage reference level. Data in and data out lines 206 from RAM 112 are also provided to computer 200. The output of computer 200 can be provided to a display 208 or a printer 210. Computer 200 also controls the operation of a light source 212.

Thus, computer 200 can synchronize the operations of the present invention to refresh RAM 112 immediately before turning on light source 212. Sequencer 180 can then be controlled to cause a reading of the memory cells in RAM 112 at specified periods of time after light source 212 has been activated. In addition, or alternately, the voltage reference can be adjusted for readings at a fixed period of time using voltage reference level generator 202.

Figure 6:
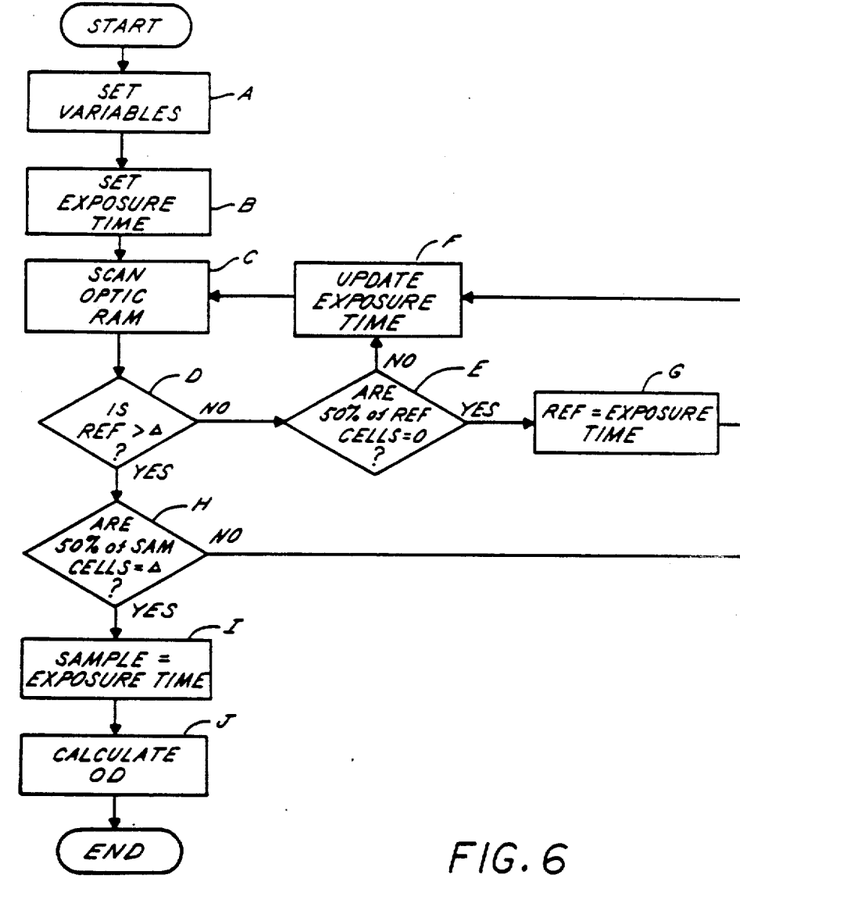
FIG. 6 is a flow chart of a sample program for operating a system in accordance with the teachings of this invention.

FIG. 6 gives an example of one type of a program which can be used to operate computer 200 for determining the optical density (OD) of a sample (SAM) on a reference background (REF). The program operates to calculate the amount of time for one-half of the memory cells in the REF portion of the RAM to change from a logic 1 to a logic 0. This read time is compared to the amount of time required for half of the memory cells in the sample area to change from a logical 1 to a logical 0. From this time value, the optical density can be calculated. Many other programs could be used, including programs which vary the voltage reference level for a fixed time.

The variables are first initialized (step A). The exposure time is then set (step B). The exposure time resolution is typically 1 millisecond (ms). The optical RAM 112 is then scanned (step C) and the computer determines whether or not a reference level has been established (step D). If not, the program will determine whether half of the referenced memory cells have discharged from logic 1 to a logic 0 (step E). If not, exposure time is updated to take a second reading (step F) and steps C, D, and E are then repeated. When half of the memory cells have changed to a logic 0, the relative darkness of the reference area is set to the last exposure time (step G). The program will go on to examine whether half of the memory cells for the sample area are discharged to a logic 0 (step H) with successive exposure time trials. When half of the memory cells for the sample memory cells have discharged, the relative darkness of the sample area is set to the last exposure time (step I). The optical density can then be calculated (step J) according to the formula:

$$OD = \log_{10}(SAM\ exposure\ time/REF\ exposure\ time)$$

This is an example of only one possible program for one possible application utilizing the present invention.

Figure 7:
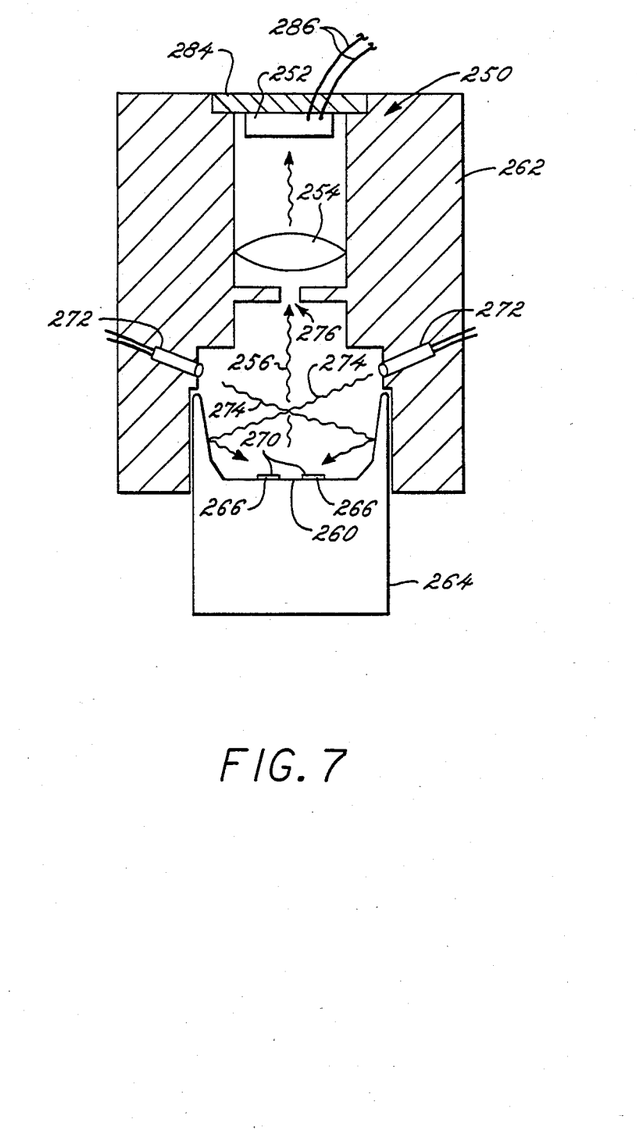
FIG. 7 is an embodiment of the subject invention for use with an ICON or similar device.

In FIG. 7, an embodiment is depicted which can be used with an ICON (available from Hybritech, San Diego, Calif.). The ICON is exemplary of devices where chemistry is performed on a surface resulting in one or more light modulating spots being formed. The device 250 has an optic RAM 252 and an aspheric lens 254 for focusing the light rays 256 reflected from surface 260 through orifice 276 onto optic RAM 252. Assay sites 266 have dye 270 deposited in relation to the amount of analyte in the sample. Light source 272 provides light rays 274. Light source 272 is preferably 8 LED's around the circumference of cylinder 262. The optic RAM 252 is mounted in an opaque cover 284 and connected to a circuit (not shown) by wires 286. Alternatively, the reaction is not terminated and the computer directs the reader to take successive readings, so that the reaction may be following kinetically.

In an example of carrying out an assay, the unknown sample is spotted at one of the sites 266 and a sample having a known amount of analyte is spotted at the other site. Reagents are added to produce a colored dye in proportion to the amount of analyte present. The reaction, if any, is terminated and the ICON 264 mounted onto device 250. The two spots 270 may then be read and the unknown value compared to the standard.

Figure 8:
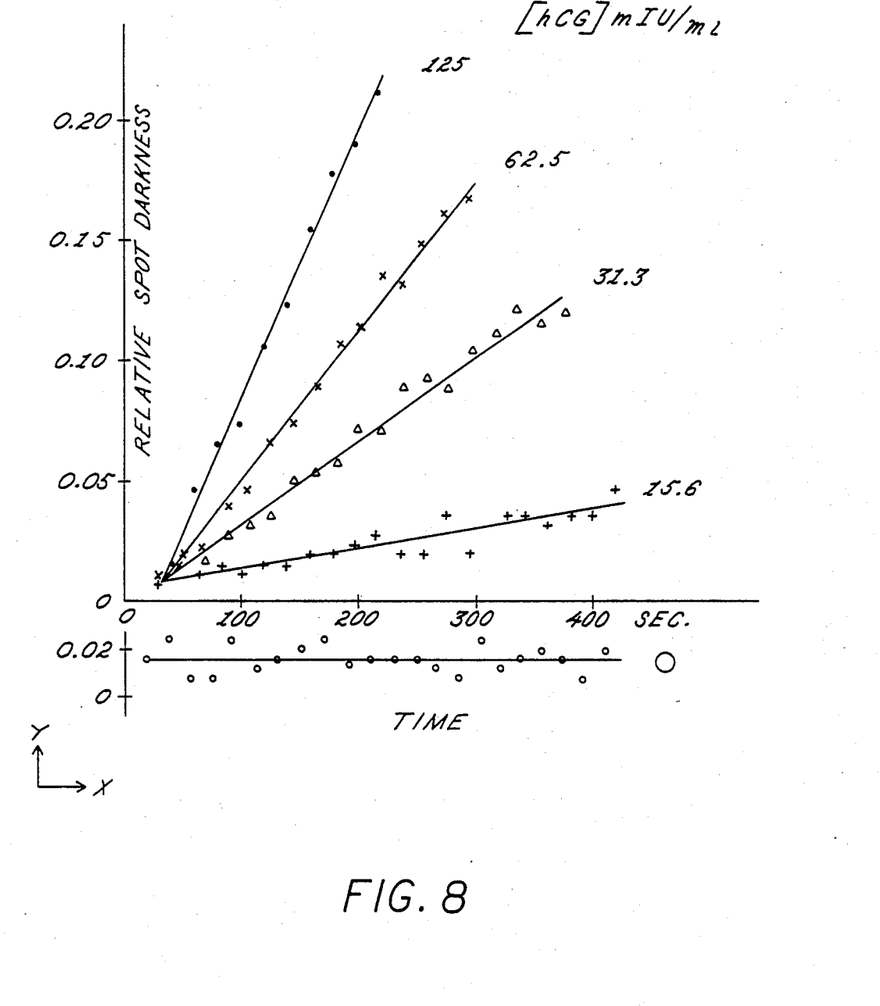
FIG. 8 is a graph of time versus relative spot darkness for the state of concentrations of a sample using measurements made with an apparatus in accordance with the teachings of this invention.

The experimental results of measurements performed using the system of FIG. 7 are set forth in FIG. 8. Various concentrations of hCG (human chorionic gonadotropin) in a buffer solution of 0.15 M NaCl, 5 mM P0$_4$(pH 6.8), 0.2% BSA, 0.01% NaN$_3$ were measured. The hCG used was Stock No. CG-2 from Sigma Chemical Company, lot 64F-0847. Five drops of the solution were placed on the center of surface 260. Three drops of an antibody conjugate were then added 5–10 seconds later. The antibody conjugate used was 8 ml of mouse monoclonal IgG (anti-hCG) conjugated to bovine alkaline phosphatase, protein matrix, and 0.1% sodium azide. A wash solution of 8 ml of buffer and 0.3% sodium azide was added one minute later up to the ICON's ridged fill line and allowed to drain. Three drops of a substrate reagent (8 ml of substrate, stabilizers, and 0.1% sodium azide) were then added. The ICON was immediately placed in the reading device and measured kinetically.

Two reference spots on surface 260 (R$_1$ and R$_2$) were used. Readings were taken every 20 seconds (x axis of FIG. 8). The relative spot darkness plotted on the y axis of FIG. 8 is $$\log \left| \frac{2t_s}{t_{R1} + t_{R2}} \right|$$

where:
 $t_s$ = time for 50% of the sample bits to change state;
 $t_{R1}$ = time for 50% of the R$_1$ reference bits to change state; and
 $t_{R2}$ = time for 50% of the R$_2$ reference bits to change state.

Concentrations of 125, 62.5 and 31.3 mIV/ml as well as a 0 concentration reference were measured. The small amount of noise for the 0 concentration control demonstrates that the device according to the present invention can measure concentrations much smaller than those set forth in FIG. 8.

The subject apparatus and methods provide for a simple and rapid determination of a wide variety of analytes. Chemistries which have already been developed may be employed, so long as a light-modulating material may be bound at a particular site in sufficient amount so as to be detectable by the dynamic RAM. By defining a particular region to be associated with a sample, the amount or other characteristics of a light-modulating material present in that region may be quantified and related to standards, so as to evaluate the amount of analyte in the sample. A large number of samples may be simultaneously determined in view of the large number of blocks of memory cells which may be addressed with a single microchip. Of course, with appropriate optics, two or more microchips may be employed which would expand the number of simultaneous determinations.

Furthermore, great sensitivity can be achieved by either varying threshold values or scanning times, or both, so that a sensitive gray scale can be obtained, which can be used to read the uneven distribution of the light-modulating material over the defined region. Also, the assay can be performed on a wide variety of uneven surfaces, since the reflected or transmitted light will be proportional to the amount of light-modulating material present on the surface. Transparent or translucent surfaces can be employed, which not only include solid surfaces, such as cellulose and nitrocellulose surfaces, but also gels which are involved with separation techniques, such as electrophoresis, immunoelectrophoresis, and the like.

Another possible method for producing a gray scale is using a multiple lens system in which a number of lenses are formed on a single piece of plastic to project the image from a single sample at a series of sites on the optic RAM. A number of gray scale filters could be placed adjacent the monolithic multiple lens so that the image from each lens passes through a different filter. The blocks of memory cells corresponding to each image could then be examined to determine the amount of light impinging on each of the blocks corresponding to each of the gray filters. Color information can also be obtained by using various color filters and comparing the readings of the different blocks of memory cells.

Although the foregoing invention has been described in som detail by way of illustration and example for purposes of clarity of understanding, it will be obvious that certain changes and modifications may be practiced within the scope of the appended claims.

What is claimed is:

1. An apparatus for determining a characteristic of an analyte in a sample by measuring the light transmitted from an assay site in relation to the amount of signal modulating component present at said assay site, wherein the amount of said component is related to the presence of said analyte in said sample, said apparatus comprising:
 means for irradiating an assay site and a standard reference site with light while correcting for any nonuniformity in the light;
 a dynamic random access memory;
 means for directing light from said sites onto a first and a second group of memory cells, respectively, of said dynamic random access memory;
 means for exposing said memory cells to said directed light for a predetermined period of time;
 means for measuring the states of said memory cells after said exposure of said group of memory cells;
 means for comparing said measured states of said first group and said second group; and
 means for analyzing said compared states to determine said characteristic of said analyte.

2. The apparatus of claim 1 further comprising means for measuring the state of said memory cells at a plurality of different times to produce a gray scale.

3. The apparatus of claim 1 further comprising means for varying a reference voltage of said memory cells so that the sensitivity to light of said memory cells is varied.

4. The apparatus of claim 3 further comprising means for adjusting said reference voltage to a plurality of levels and means for measuring the states of said memory cells at each of said levels to produce a gray scale.

5. The apparatus of claim 1 further comprising means for focussing said light from said assay and reference sites onto said group of memory cells.

6. The apparatus of claim 1 further comprising means for irradiating a plurality of assay sites simultaneously and means for directing light from each said assay site to a different one of a plurality of groups of memory cells of said dynamic random access memory.

7. The apparatus of claim 1 further comprising means for changing the memory cells composing said group so that light from said assay site is substantially centered in said group.

8. An apparatus for determining a characteristic of a plurality of analytes in a plurality of samples by measuring the light transmitted from a plurality of assay sites on a solid support in relation to the amount of signal modulating component present at each said assay site, wherein the amount of said component is related to the presence of analyte in a sample, said apparatus comprising:
- a light source for uniformly directing light to a plurality of assay sites and to a reference site;
- a dynamic random access memory having a plurality of memory cells, said memory having an exposed surface covered by a light-transmitting non-reflective plate;
- a lens for focussing light from each said site onto a separate block of said memory cells;
- a sequencer for sequentially reading said memory cells after a predetermined exposure time;
- means for comparing the states of said memory cells for each said block;
- means for comparing said measured states for a reference site block to each of the other blocks; and
- means for analyzing said compared states to determine said characteristic of said analytes.

9. The apparatus of claim 8 further comprising a computer for controlling the operation of said apparatus and analyzing the states of said memory cells.

10. The apparatus of claim 8 further comprising a plurality of lenses arranged to focus an image from a single site onto a plurality of blocks of memory cells on said dynamic random access memory and a plurality of filters, each filter being arranged to filter an image projected by one of said lenses onto one of said blocks of memory cells.

11. The apparatus of claim 8 further comprising means for applying reagents to said sites on said solid support.

12. A method for determining a characteristic of an analyte in a sample, said method comprising the steps of:
- irradiating an assay site and a standard reference site with light while correcting for any non-uniformity in the light;
- directing light from said sites onto a first and a second group of memory cells, respectively, of a dynamic random access memory;
- exposing said memory cells to said directed light for a predetermined period of time;
- measuring the states of said memory cells after said exposure of said group of memory cells;
- comparing said measured states of said first group and said second group; and
- analyzing said compared states to determined said characteristic of said analyte.

13. The method of claim 12 wherein said step for measuring the state of said memory cells is performed at a plurality of different times to produce a gray scale.

* * * * *

UNITED STATES PATENT AND TRADEMARK OFFICE
CERTIFICATE OF CORRECTION

PATENT NO. : 4,737,464

Page 1 of 3

DATED : April 12, 1988

INVENTOR(S) : Harden M. McConnell, et al.

It is certified that error appears in the above-identified patent and that said Letters Patent is hereby corrected as shown below:

The sheets of Drawings consisting of Figs. 5 and 6 should be inserted as per attached sheets.

Signed and Sealed this

Fourteenth Day of August, 1990

Attest:

HARRY F. MANBECK, JR.

Attesting Officer

Commissioner of Patents and Trademarks

FIG. 5

FIG. 6